United States Patent [19]

Knaus et al.

[11] 4,088,653
[45] May 9, 1978

[54] TETRAHYDROPYRIDYL DERIVATIVES

[75] Inventors: Edward E. Knaus; Kinfe Redda, both of Edmonton; Frank Wilhelm Wandelmaier, Montreal, all of Canada

[73] Assignee: Canadian Patents and Developments Limited, Ottawa, Canada

[21] Appl. No.: 716,676

[22] Filed: Aug. 23, 1976

[51] Int. Cl.$^2$ .................. C07D 401/12; A61K 31/44
[52] U.S. Cl. .................... 260/295 AM; 260/295.5 A; 424/263
[58] Field of Search ............... 260/295 AM, 295.5 A; 424/263

[56] References Cited
U.S. PATENT DOCUMENTS 4,021,224  5/1977  Pallos et al. ........................... 71/88

Primary Examiner—Donald G. Daus
Assistant Examiner—Lisa Jones
Attorney, Agent, or Firm—W. Charles Kent

[57] ABSTRACT

Pharmaceutical compounds of the general formula

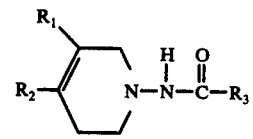

and non-toxic pharmaceutically acceptable salts thereof, wherein $R_1$ and $R_2$ are selected from the group consisting of hydrogen, lower alkyl having from 1 to 4 carbon atoms, lower alkoxy having from 1 to 4 carbon atoms and hydroxy lower alkyl having from 1 to 4 carbon atoms, and if $R_1$ or $R_2$ is other than hydrogen, the other substituent is hydrogen; and $R_3$ is a member selected from the group consisting of pyridyl, phenyl, lower alkyl substituted pyridyl, lower alkoxy substituted pyridyl, lower alkyl substituted phenyl and lower alkoxy substituted phenyl, the lower alkyl and alkoxy substituents having from 1 to 4 carbon atoms. These compounds exhibit an analgesic, hyperglycemic or anti-inflammatory activity.

19 Claims, No Drawings

TETRAHYDROPYRIDYL DERIVATIVES

DESCRIPTION OF THE INVENTION

The present invention relates to pharmaceutical compounds. More particularly, the invention provides novel tetrahydropyridyl derivatives or non-toxic pharmaceutically acceptable salts thereof having particular physiological effects. The invention relates to such compounds and compositions thereof, and to processes for making and using them.

The novel tetrahydropyridyl derivatives of the present invention have a structural formula

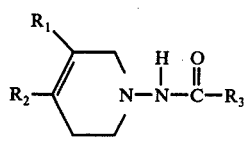

and non-toxic pharmaceutically acceptable salts thereof, wherein $R_1$ and $R_2$ are selected from the group consisting of hydrogen, lower alkyl, lower alkoxy, and hydroxy lower alkyl, and if $R_1$ or $R_2$ is other than hydrogen, the other substituent is hydrogen;

and $R_3$ is a member selected from the group consisting of pyridyl, phenyl, lower alkyl substituted pyridyl, lower alkoxy substituted pyridyl, lower alkyl substituted phenyl and lower alkoxy substituted phenyl. In this specification, it will be understood that "lower alkyl" and "lower alkoxy" substituents mean those having from 1 to 4 carbon atoms. These compounds exhibit an analgesic, hyperglycemic or anti-inflammatory activity. Non-toxic pharmaceutically acceptable salts thereof are also within the scope of the present invention.

These tetrahydropyridyl derivatives are prepared by reacting a carbonylhydrazide of the formula:

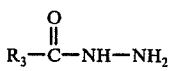

wherein $R_3$ is a member selected from the group consisting of pyridyl, phenyl and lower alkyl substituted or lower alkoxy substituted pyridyl or phenyl, with an arylpyridinium halide of structural formula:

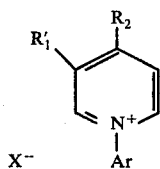

wherein $R_1$ and $R_2$ are selected from the group consisting of hydrogen, lower alkyl, lower alkoxy, and hydroxy lower alkyl, and if $R_1$ or $R_2$ is other than hydrogen, the other substituent is hydrogen, Ar represents an aryl or substituted aryl group, and X is Cl, Br or I, heating the product sufficiently to convert to N-(pyridylcarbonylimino) ylide of the formula:

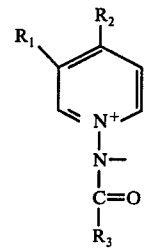

wherein $R_1$, $R_2$ and $R_3$ are as defined above, and converting this pyridinium ylide in the presence of a suitable reducing agent to a corresponding tetrahydropyridyl derivative.

More particularly, the following compounds have been prepared, and through testing, have been found to have the following physiological activity:

| Name | Designation | Physiological Activity |
| --- | --- | --- |
| N-(4-pyridylcarbonylimino)-1,2,5,6-tetrahydropyridine | A13 | analgesic, hyperglycemic anti-inflammatory |
| N-(3-pyridylcarbonylimino)-1,2,5,6-tetrahydropyridine | A14 | analgesic, hyperglycemic |
| N-(2-pyridylcarbonylimino)-1,2,5,6-tetrahydropyridine | A19 | analgesic, hyperglycemic anti-inflammatory |
| N-(benzoylimino)-1,2,5,6-tetrahydropyridine | A20 | analgesic and anti-inflammatory |
| N-(benzoylimino)-3-(3¹-hydroxypropyl)-1,2,5,6-tetrahydropyridine | A21 | analgesic (slight) |
| N-(4-pyridylcarbonylimino)-3-(3¹-hydroxypropyl)-1,2,5,6-tetrahydropyridine | A22 | analgesic (slight) |
| N-(4-pyridylcarbonylimino)-4-(3¹-hydroxypropyl)-1,2,5,6-tetrahydropyridine | A23 | anti-inflammatory |

Suitable pharmaceutically acceptable salt forms of these compounds include alkaline metal salts, for example the potassium or sodium salt, and the ammonium salt, and alkaline earth metal salts, e.g. the calcium salt, as well as the mineral acid salts, for example the hydrochloride and hydrobromide salts.

These compounds can be administered either parenterally, as by injection, or orally. As a liquid carrier, a carrier such as water, ethyl alcohol or polyethylene glycol, or other physiologically acceptable solvents or dispersing liquids can be used. For oral administration, either solid or liquid carriers may be used. One commonly used solid carrier is gum acacia, but others are also suitable.

The following non-limitative examples illustrate some selected methods for producing the compounds according to the present invention, as well as comparative data illustrating the therapeutic effect of representative compounds according to the present invention.

PREPARATION

EXAMPLE 1

N-(4-pyridylcarbonylimino)-1,2,5,6-tetrahydropyridine (A-13)

(See schematic representation following example)

2,4-Dinitrophenylpyridinium chloride I (6.52 g, 0.02316 mol) is dissolved in 20 ml of methanol and the solution is cooled to 0° C. A suspension of isonicotinic acid hydrazide II (6.2 g, 0.04526 mol) in 60 ml of methanol is added to the cooled solution in five portions from an addition funnel while stirring continuously. Triethylamine (1.8 ml) is added and the reaction mixture is stirred at room temperature for 12 hours. The solid which precipitates III is filtered off and washed with 60 ml each of methanol, water, methanol and ether in this order. This washed solid III is suspended in 150 ml of a dioxane-water mixture (4:1 ratio) and the suspension is boiled under reflux for 12 hours to afford a clear solution. The solvent is evaporated under reduced pressure. Water (150 ml) is added to the residue and the insoluble material is filtered off. Evaporation of the solvent from the filtrate above afforded 3.18 g (69%) of N-(4-pyridylcarbonylimino)pyridinium ylide IV which can be purified further by elution from a 2.5 × 25 cm neutral alumina column using 625 ml methanol-ether (1:5 ratio) to give 2.3 g IV as a light yellow crystalline solid with mp 219°–221° C.

Sodium borohydride (0.7 g) is added to 60 ml of 95% ethanol pre-cooled to 0° C. A solution of N-(4-pyridylcarbonylimino)pyridinium ylide IV (2.138 g, 0.01074 mol) dissolved in 30 ml of 95% ethanol is then added dropwise with continuous stirring. The reaction is maintained at 0° C for 4 hours after which the reaction mixture is poured onto 100 g of crushed ice and allowed to stand at room temperature for 30 minutes. This solution is then extracted with chloroform (4 × 50 ml), the chloroform extract is dried (Na$_2$SO$_4$) and filtered. The solvent is removed from the filtrate at reduced pressure to give 2.0 g (92%) of N-(4-pyridylcarbonylimino)-1,2,5,6-tetrahydropyridine V (A-13) which can be purified further by elution from a 2.5 × 25 cm neutral aluminum column using 500 ml of ether-methanol (5:1 ratio) to give 1.854 g V as a white-yellow crystalline solid with mp 141°–144° C. The structure V assigned to N-(4-pyridylcarbonylimino)-1,2,5,6-tetrahydropyridine is in agreement with its infrared (IR), mass spectral (MS) and nuclear magnetic resonance (NMR) spectra. Mass Spectra (70 ev): Mass calc'd for C$_{11}$H$_{13}$N$_3$O: 203.1059; Found: 203.1056.

SCHEMATIC FOR EXAMPLE 1

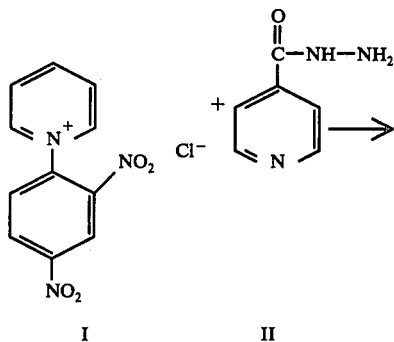

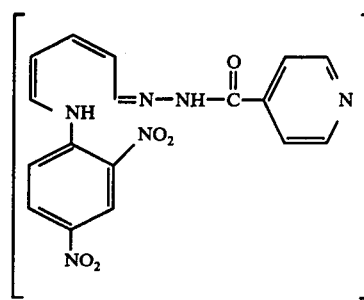

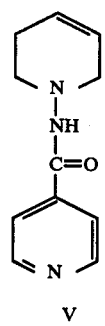 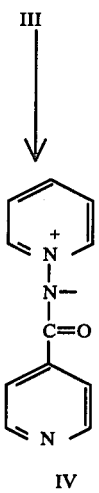

V        IV

EXAMPLE 2

N-(3-pyridylcarbonylimino)-1,2,5,6-tetrahydropyridine (A-14)

(See schematic representation following example)

2,4-Dinitrophenylpyridinium chloride 1 (3.26 g, 0.01158 mol) is dissolved in 20 ml of methanol and the solution is cooled to 0° C. A suspension of nicotinic acid hydrazide VI (3.1 g, 0.02263 mol) in 60 ml of methanol is added to the cooled solution in five portions from an addition funnel while stirring continuously. Triethylamine (0.9 ml) is added and the reaction mixture is stirred at room temperature for 12 hours. The solid which precipitates VII is filtered off and washed with 60 ml each of methanol, water, methanol and ether in this order. This washed solid VII is suspended in 150 ml of a dioxane-water mixture (4:1 ratio) and the suspension is boiled under reflux for 12 hours to afford a clear solution. The solvent is evaporated under reduced pressure. Water (150 ml) is added to the residue and the insoluble material is filtered off. Evaporation of the solvent from the filtrate above afforded 1.52 g (66%) of N-(3-pyridylcarbonylimino) pyridinium ylide VIII which can be purified further by elution from a 2.5 × 25 cm alumina column using 250 ml of methanol-ether (1:6 ratio) to give 1.062 g VIII as a pale yellow crystalline solid, mp 167°–169° C.

Sodium borohydride (0.6 g) is added to 20 ml of 95% ethanol pre-cooled to 0° C. A solution of N-(3-pyridylcarbonylimino) pyridinium ylide VIII (1.752 g, 0.0088 mol) dissolved in 30 ml of 95% ethanol is then added dropwise with continuous stirring. The reaction is maintained at 0° C for 5 hours after which the reaction mixture is poured onto 100 g of crushed ice and allowed to stand at room temperature for 30 minutes. This solution is then extracted with chloroform (4 × 50 ml), the chloroform extract is dried (Na$_2$SO$_4$) and filtered. The solvent is removed from the filtrate at reduced pressure to give 1.77 g (99%) of N-(3-pyridylcarbonylimino)-1,2,5,6-tetrahydropyridine IX (A-14) which can be purified further by elution from a 2.5 × 25 cm neutral alumina column using 300 ml of methanol-ether (1:6 ratio) to give 1.433 g of IX as yellowish-white solid with mp 119°–121° C. The structure IX assigned to N-(3-pyridylcarbonylimino)-1,2,5,6-tetrahydropyridine is in agreement with its infrared (IR), mass spectral (MS) and nuclear magnetic resonance spectra (NMR). Mass Spectra (70 ev): Mass Calc'd for C$_{11}$H$_{13}$N$_3$O: 203.1059; Found: 203.1062.

EXAMPLE 3

Related N-(substituted-carbonylimino)-1,2,5,6-tetrahydropyridines have been prepared as shown in the schematic representation below using equivalent quantities of other carbonylhydrazides XI using procedures similar to those outlined in the preceding examples. The melting point for each product prepared is set out in Table 1.

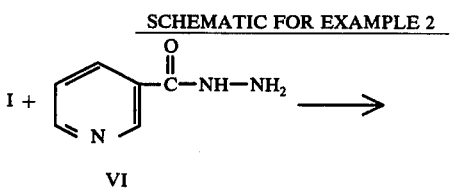

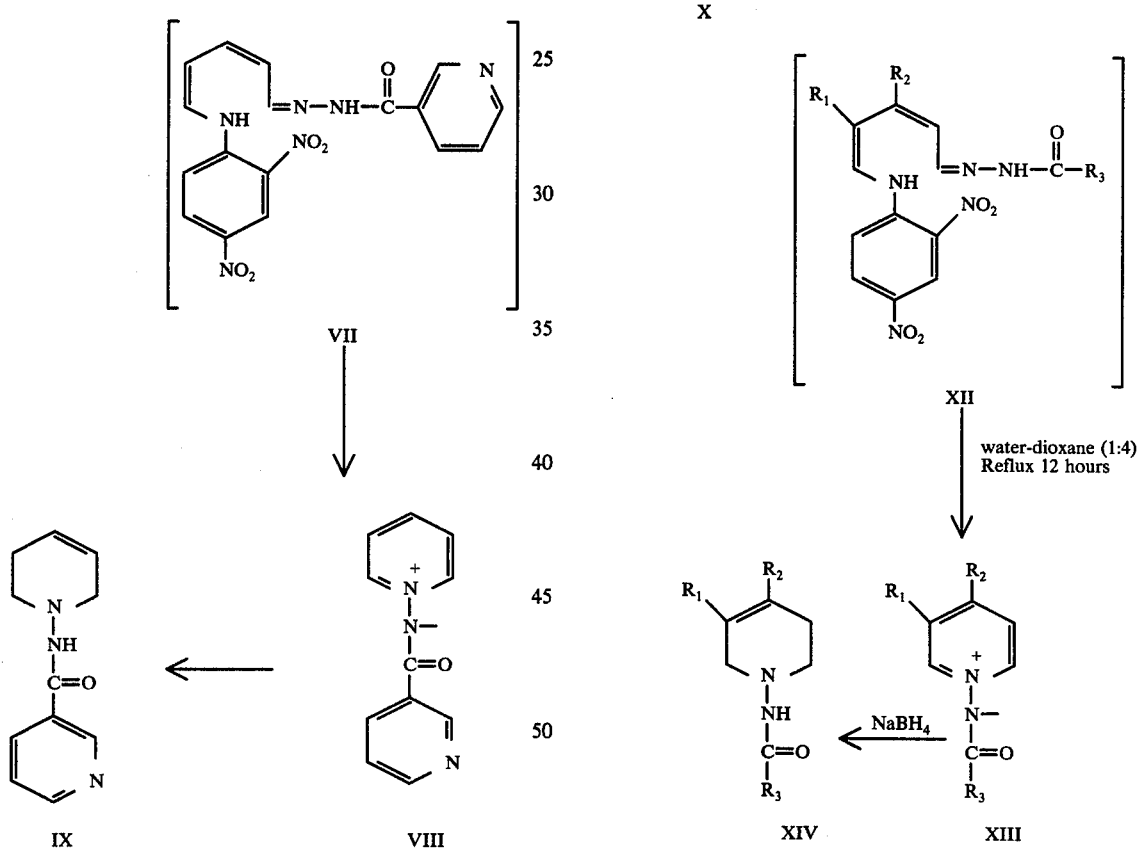

TABLE 1

| N-(substituted-carbonylimino)-1,2,5,6-tetrahydropyridines prepared according to Example 3. | | | | | |
|---|---|---|---|---|---|
| Chemical Name | Designation | R$^1$ | R$^2$ | R$^3$ | MP |
| N-(2-pyridylcarbonylimino)-1,2,5,6-tetrahydropyridine | A-19 | H | H | (2-pyridyl) | 82–83° |
| N-(benzoylimino)-1,2,5,6-tetrahydropyridine | A-20 | H | H | (phenyl) | 126–128° |

TABLE 1-continued

N-(substituted-carbonylimino)-1,2,5,6-tetrahydropyridines prepared according to Example 3.

| Chemical Name | Designation | $R^1$ | $R^2$ | $R^3$ | MP |
|---|---|---|---|---|---|
| N-(benzoylimino)-3-($3^1$-hydroxypropyl-1,2,5,6-tetrahydropyridine | A-21 | —(CH$_2$)$_3$OH | H | 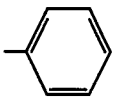 | 157–159° |
| N-(4-pyridylcarbonylimino)-3-($3^1$-hydroxypropyl)-1,2,5,6-tetrahydropyridine | A-22 | —(CH$_2$)$_3$OH | H | 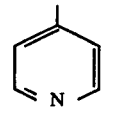 | 142–144° |
| N-(4-pyridylcarbonylimino)-4-($3^1$-hydroxypropyl)-1,2,5,6-tetrahydropyridine | A-23 | H | —(CH$_2$)$_3$OH | 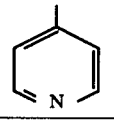 | 167–169° |

BIOLOGICAL TESTING

Initially the activity of the compound tested on an animal was determined at a single dose. If the substance was active at this dose, it was subjected to limited repeat testing. If the presence of activity was confirmed by repetition of the testing, a dose response relation was constructed and the effective dose (ED$_{50}$) determined. If toxicity was encountered with the initial dose, the dose was reduced until one was reached which was tolerated by the animals tested.

EXAMPLE 4

Analgesic Activity

Substances were administered subcutaneously to Swiss albino mice, weighing 18 to 22 grams, before determining their activity in the phenylquinone-writhing test (Collier et al., Br. J. Pharmacol. Chemotherap. 32: 295, 1968). The active ingredients were suspended in a solution of physiological saline and "Tween 80" (TM) surfactant. A dose amounting to 10 milliliters of physiological saline solution and active ingredient per kilogram of bodyweight was administered to the mice according to the dosage as set out in Table 2. The test results are shown in Table 2, the compounds tested being compared to Aspirin (TM).

TABLE 2

Analgesic activity of tetrahydropyridine derivates tested.

| Substance | Dose mg/kg | No. Animals | Response % inhibition | Ed$_{50}$* mg/kg | 95% confidence limits |
|---|---|---|---|---|---|
| A-13 | 32 | 5 | 38.6 | | (29.4–95.4) |
|  | 64 | 5 | 58.0 | 53 |  |
|  | 128 | 5 | 80.8 |  |  |
|  | 256 | 5 | 96.0 |  |  |
| A-14 | 32 | 5 | 38.9 |  |  |
|  | 64 | 5 | 59.2 | 47 | (18.1–122.2) |
|  | 128 | 5 | 81.2 |  |  |
|  | 256 | 5 | 89.6 |  |  |
| A-19 | 128 | 15 | 57.3 |  |  |
| A-20 | 16 | 5 | 26.2 |  |  |
|  | 32 | 5 | 57.4 |  |  |
|  | 64 | 5 | 59.0 | 36 | (15.6–82.8) |
|  | 128 | 15 | 88.2 |  |  |
|  | 256 | 5 | 98.0 |  |  |
| A-21 | 128 | 10 | 20 |  |  |
| A-22 | 128 | 10 | 43 |  |  |
| A-23 | 128 | 5 | 11 |  |  |
| Standard: Aspirin (TM) |  |  |  | 52 | (34.6–78.0) |

*Determined by the method of Litchfield and Wilcoxon (J. Pharmacol. Exp. Therap. 96: 99, 1949)

Compounds A-13, A-14, A-19 and A-20 appear as active analgesics, comparing with the standard compound Aspirin (TM).

EXAMPLE 5

Anti-inflammatory activity

Substances were administered subcutaneously to Sprague-Dawley rats, weighing 100–120 g. A suspension of 0.03% carageenan was injected under the plantar skin of a hind paw. The increase in volume of the inflamed paw was measured 3 and 5 hours after drug administration. The percent of animals with significantly lower inflamed paw volumes than the untreated control animals was calculated. (Winter C.A. (1965) in International Symposium on Non-Steroidal pp 190–202, Excerpta Medica Foundation, Amsterdam).

The test results are shown in Table 3.

TABLE 3

Anti-inflammatory activity of tetrahydropyridine derivatives.

| Substance | Dose mg/kg | No. of Animals | Response % 3 hours... | animals protected 5 hours after drug |
|---|---|---|---|---|
| A-13 | 64 | 4 | 25 | 75 |
| A-14 | 64 | 4 | 50 | 0 |
| A-19 | 64 | 4 | 25 | 75 |
| A-20 | 64 | 4 | 25 | 50 |
| A-23 | 64 | 4 | 25 | 75 |
| Standard: Indomethazine (TM) | 12 | 4 | 50 | 50 |

A-13, A-19 and A-23 show a striking anti-inflammatory action, comparing favourably with the standard compound used.

EXAMPLE 6

Determination of blood-glucose

Substances were suspended in distilled water and were administered orally to over-night fasted Wistar rats. Capillary blood samples were obtained from the tail at 0, 2 and 4 hours post-treatment and the sera derived from these samples were analyzed for glucose by spectrophotometric determination of enzymatically produced NADH$_2$. (Escalab ® G:15) (Barthelmai and Czok, Klinische Wochenschrift 40: 585 (1962)). The test results are shown in Table 4.

TABLE 4

Hyperglycemic activity of compounds tested.

| Substance | Dose mg/kg | % change in blood-glucose concentrations Post-Treatment | |
|---|---|---|---|
|  |  | 20 hours | 4 hours |
| A-13 | 50 | +20 | — |
|  | 100 | +80 |  |

TABLE 4-continued

| | | % change in blood-glucose concentrations Post-Treatment | |
|---|---|---|---|
| Substance | Dose mg/kg | 20 hours | 4 hours |
| | 200 | +240 | — |
| A-14 | 200 | +60 | — |
| A-19 | 100 | +50 | +50 |
| | 200 | +50 | +50 |

A-13, A-14 and A-19 have demonstrated hyperglycemic activity in these tests.

We claim as our invention:
1. A tetrahydropyridine of the formula:

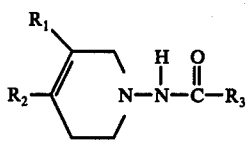

(I)

or a non-toxic pharmaceutically acceptably salt thereof, wherein $R_1$ and $R_2$ are selected from the group consisting of hydrogen, lower alkyl, lower alkoxy, and hydroxy lower alkyl, and if $R_1$ or $R_2$ is other than hydrogen, the other substituent is hydrogen; and $R_3$ is a member selected from the group consisting of pyridyl, phenyl, and lower alkyl substituted or lower alkoxy substituted pyridyl or phenyl.

2. A tetrahydropyridine as defined in claim 1, wherein $R_1$ and $R_2$ are each hydrogen or —$(CH_2)_3OH$, and if $R_1$ or $R_2$ is —$(CH_2)_3OH$, the other substituent is hydrogen; and $R_3$ is a substituent selected from the group consisting of pyridyl and phenyl.

3. N-(4-pyridylcarbonylimino)-1,2,5,6-tetrahydropyridine, according to claim 2.

4. N-(3-pyridylcarbonylimino)-1,2,5,6-tetrahydropyridine, according to claim 2.

5. N-(2-pyridylcarbonylimino)-1,2,5,6-tetrahydropyridine, according to claim 2.

6. N-(benzoylimino)-1,2,5,6-tetrahydropyridine, according to claim 2.

7. N-(benzoylimino)-3-(3$^1$-hydroxypropyl)-1,2,5,6-tetrahydropyridine, according to claim 2.

8. N-(4-pyridylcarbonylimino)-3-(3$^1$-hydroxypropyl)-1,2,5,6-tetrahydropyridine, according to claim 2.

9. N-(4-pyridylcarbonylimino)-4-(3$^1$-hydroxypropyl)-1,2,5,6-tetrahydropyridine, according to claim 2.

10. The compound of claim 1 in a pharmaceutical carrier, sufficient active compound being present so that the composition has at least one of analgesic, hyperglycemic and anti-inflammatory activity.

11. The compound of claim 2 in a pharmaceutical carrier, sufficient active compound being present so that the composition has at least one of analgesic, hyperglycemic and anti-inflammatory activity.

12. The composition of claim 10, wherein the pharmaceutical carrier is a liquid carrier suitable for injection.

13. The composition of claim 11, wherein the pharmaceutical carrier is a solid or liquid suitable for oral administration.

14. The composition of claim 11, wherein the carrier is an aqueous liquid.

15. A method of preparing a tetrahydropyridine derivative of structural formula 1 as defined in claim 1 which comprises reacting in a methanol solvent at room temperature a carbonylhydrazide of the formula:

(II)

wherein $R_3$ is as defined in claim 1, with an arylpyridinium halide of structural formula:

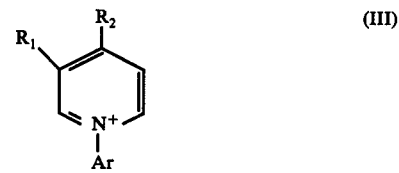

(III)

wherein $R_1$ and $R_2$ are as defined in claim 1, Ar represents an aryl or substituted aryl group, and X is Cl, Br, or I, heating the product at reflux temperatures in dioxane/water sufficiently to convert to N-(pyridylcarbonylimino) ylide of the formula:

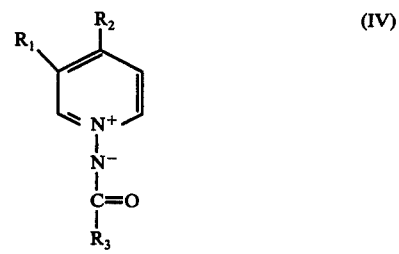

(IV)

wherein $R_1$, $R_2$ and $R_3$ are as defined above, and converting the pyridinium ylide of formula IV at a temperature of 0° C in an ethanol solvent in the presence of a borohydride reducing agent to a substituted carbonylimine of the formula I.

16. A method according to claim 15, for preparing a tetrahydropyridine I wherein $R_1$ and $R_2$ are each hydrogen or —$(CH_2)_3OH$, and if $R_1$ or $R_2$ is —$(CH_2)_3OH$, the other substituent is hydrogen; and $R_3$ is a member selected from the group consisting of pyridyl and phenyl.

17. A method of preparing a tetrahydropyridine according to claim 15 which comprises reacting a carbonylhydrazide of the formula II as defined in claim 15 with a dinitrophenyl pyridinium chloride of structural formula III wherein $R_1$ and $R_2$ are as defined in claim 15.

18. A method according to claim 17, wherein the product of the reaction of the carbonylhydrazide of the formula II with the dinitrophenyl pyridinium chloride of structural formula III is converted under reflux to N-(pyridylcarbonylimino) ylide IV.

19. A method according to claim 18, wherein the N-(pyridylcarbonylimino)ylide IV produced is converted to the tetrahydropyridyl in the presence of sodium borohydride.

* * * * *